(12) United States Patent
Antonette (10) Patent No.: US 12,410,998 B2
(45) Date of Patent: Sep. 9, 2025

(54) VALVETRAIN TESTING USING INSTRUMENTED PUSHROD

(71) Applicant: Textron Innovations, Inc., Providence, RI (US)

(72) Inventor: Kyle Louis Antonette, Williamsport, PA (US)

(73) Assignee: Textron Innovations Inc., Providence, RI (US)

( * ) Notice: Subject to any disclaimer, the term of this patent is extended or adjusted under 35 U.S.C. 154(b) by 259 days.

(21) Appl. No.: 18/150,543

(22) Filed: Jan. 5, 2023

(65) Prior Publication Data

US 2023/0213325 A1 Jul. 6, 2023

Related U.S. Application Data

(60) Provisional application No. 63/296,668, filed on Jan. 5, 2022.

(51) Int. Cl.
*G01B 7/16* (2006.01)
*G01B 5/30* (2006.01)
*G01L 1/22* (2006.01)

(52) U.S. Cl.
CPC ............ *G01B 7/16* (2013.01); *G01B 5/30* (2013.01); *G01L 1/2287* (2013.01); *A61B 2562/0261* (2013.01)

(58) Field of Classification Search
None
See application file for complete search history.

(56) References Cited

U.S. PATENT DOCUMENTS

| | | | |
|---|---|---|---|
| 4,519,345 A * | 5/1985 | Walter | F01L 13/0021 123/90.39 |
| 4,926,805 A | 5/1990 | Tomlinson | |
| 5,000,137 A | 3/1991 | Weinert et al. | |
| 5,780,730 A | 7/1998 | Scourtes et al. | |
| 7,658,173 B2 | 2/2010 | Carroll et al. | |
| 7,658,184 B2 | 2/2010 | Matas et al. | |

(Continued)

FOREIGN PATENT DOCUMENTS

| | | |
|---|---|---|
| CN | 106855447 | 6/2017 |
| CN | 106855447 A * | 6/2017 |

(Continued)

OTHER PUBLICATIONS

Guo Jie et al: "Dynamic and exciting analysis with modal characteristics for valve train using a flexible model", Mechanism and Machine Theory, Pergamon, Amsterdam, NL, vol. 78, Apr. 18, 2014 (Apr. 18, 2014), pp. 158-176, XP029023722, ISSN: 0094-114X, DOI: 10.1016/J. MECHMACHTHEORY.2014.03.012, abstract, figure A2, and Appendix C.

(Continued)

*Primary Examiner* — John E Breene
*Assistant Examiner* — Nigel H Plumb
(74) *Attorney, Agent, or Firm* — BainwoodHuang (57) ABSTRACT

A technique for testing a pushrod valvetrain in an engine includes replacing an original pushrod with an instrumented pushrod (IPD) which includes a sensor configured to measure strain and/or motion. The engine is then operated, and the output of the sensor is monitored for anomalies. Diagnosis and repair of identified defects may then follow.

20 Claims, 6 Drawing Sheets

(56) References Cited

U.S. PATENT DOCUMENTS

| | | | |
|---|---|---|---|
| 7,798,012 B2* | 9/2010 | Rosen | G01B 7/31 |
| | | | 73/781 |
| 8,015,962 B2 | 9/2011 | Lysinger | |
| 8,056,518 B1 | 11/2011 | Novak et al. | |
| 8,166,805 B1 | 5/2012 | Thompson | |
| 9,644,503 B2 | 5/2017 | Zurface et al. | |
| 10,088,388 B2 | 10/2018 | Chen | |
| 2007/0293152 A1* | 12/2007 | Rosen | G01M 13/02 |
| | | | 455/39 |
| 2016/0058554 A1 | 3/2016 | Anderson et al. | |
| 2017/0306810 A1 | 10/2017 | Nielsen et al. | |
| 2020/0400042 A1 | 12/2020 | Cunningham et al. | |

FOREIGN PATENT DOCUMENTS

| | | | |
|---|---|---|---|
| JP | H1047220 A * | 2/1998 | |
| WO | 2006081873 | 8/2006 | |

OTHER PUBLICATIONS

Notification of Transmittal of the International Search Report and the Written Opinion of the International Searching Authority, for PCT application No. PCT/US2023/010218, dated May 3, 2023, 12 pages.

* cited by examiner

VALVETRAIN TESTING USING INSTRUMENTED PUSHROD

CROSS-REFERENCE TO RELATED APPLICATIONS

This application claims the benefit of U.S. Provisional Patent Application No. 63/296,668, filed Jan. 5, 2022, the contents and teachings of which are incorporated herein in their entirety.

BACKGROUND

Valvetrains are common features of internal combustion engines, where they perform the functions of opening and closing valves at appropriate times. A typical valvetrain includes a rotatable camshaft having an array of cams. Each cam is configured to push against a tappet, which is coupled through a lash adjuster and linkage to a respective valve within a combustion chamber. As the camshaft rotates, the cam presents an eccentric profile to the tappet, repeatedly pushing against the tappet and causing the valve repeatedly to open. A valve spring forces the valve to close when it is not being pushed open by the cam.

Some valvetrains use pushrods in the linkages between cams and the respective valves. Pushrod designs promote flexibility by allowing camshafts to be located some distance away from the valves that they actuate. Such designs may be found in many aviation engines, as well as in certain automotive engines and in engines used for other purposes.

As with any complex mechanical system, pushrod valvetrains are susceptible to various conditions that degrade their performance. For example, lash adjusters can improperly leak, oil contaminants can interfere with valve movement, and valve springs can become worn. To detect and diagnose these issues, various types of test equipment have been developed. One example, called the SpinTron, uses a laser to monitor moving parts inside an engine. The laser is shone on a valve inside a combustion chamber, and a camera monitors the movement of the valve in real time, allowing results to be displayed on a computer. Using the SpinTron, one can precisely identify, document, and record crucial characteristics of a valvetrain, such as valve bounce, lofting, spring harmonics, and pushrod deflection.

SUMMARY

Unfortunately, the SpinTron is an expensive piece of machinery that is beyond the means of many repair facilities. Designed more for development than for repair, the SpinTron uses an external motor to spin an unfired engine and thus does not generally identify issues related to combustion. Further still, the laser-based technique requires accessing regions inside the engine and thus involves considerable disassembly. What is needed is a testing solution which is inexpensive, requires minimal disassembly, and can be run even when operating the engine in a fired arrangement.

In contrast with the above-described prior approach, an improved technique for testing a pushrod valvetrain in an engine includes replacing an original pushrod with an instrumented pushrod (IPD) which includes a sensor configured to measure strain and/or motion (e.g., acceleration, velocity, displacement, etc.). The engine is then operated, and the output of the sensor is monitored for anomalies. Diagnosis and repair of identified defects may then be performed.

As pushrods in many configurations extend outside a main body of an engine and can easily be removed, the original pushrod can usually be replaced quickly. The same IPD can be used again and again in different engines, or for testing or characterizing different valves of a single engine. In some examples, multiple IPDs are used for testing multiple valves of an engine at the same time. As the engine is made to spin under its own power, no costly external motor is required. Material costs are expected to be modest. Also, the improved technique is amenable for use in repair and field-service facilities, where engines may be quickly tested, repaired, and returned to service.

In some examples, the technique further includes comparing output from the sensor with that of a modeled, ideal valvetrain (or with a known-good, "golden," valve train) and identifying discrepancies.

In some examples, the sensor is attached to an outer surface of the IPD. For example, the sensor may be bonded to the IPD using epoxy or some other adhesive.

In some examples, the original pushrod is configured to move in reciprocal fashion within a shroud tube, and the technique further includes replacing the shroud tube with a modified tube that includes an aperture through which wires pass between the sensor and external measurement equipment.

In some examples, the external measurement equipment is configured to receive electrical signals from sensors, to digitize such signals, and to record them for analysis and/or viewing, e.g., on a computer screen, printout, or the like.

In some examples, the aperture is a slot, and the IPD has a guide, such as a pin or tab, which extends from a side of the instrumented pushrod and into the slot. The guide resists rotation of the instrumented pushrod within the modified tube and thus prevents wrapping of wires around the IPD during operation. As the IPD moves back and forth within the modified tube, the guide moves back and forth within the slot.

In some examples, a proximity sensor is affixed to the modified tube so as to detect a position of the guide as it moves within the slot. For example, the proximity sensor is placed near an end of the slot and is aligned axially with the slot so that it is able to monitor the position of the guide as it moves back and forth. In an example, the proximity sensor is an electromagnetic sensor, such as an inductive sensor if the guide is made of metallic material (e.g., steel), or a capacitive sensor if the guide is non-metallic (e.g., plastic).

In some examples, the sensor includes a strain gauge oriented axially with the instrumented pushrod so as to measure axial strain.

In some examples, the strain gauge is a first strain gauge and the sensor further includes a second strain gauge oriented perpendicularly to the first strain gauge. In such cases, the technique may further include adjusting a strain signal from the first strain gauge based on a signal from the second strain gauge so as to compensate the strain signal for temperature variations.

Certain embodiments are directed to an instrumented pushrod. Other embodiments are directed to a method of testing or characterizing a valvetrain of an engine. Still other embodiments are directed to a method of compensating for effects of high temperature when using an instrumented pushrod.

The foregoing summary is presented for illustrative purposes to assist the reader in readily grasping example features presented herein; however, this summary is not intended to set forth required elements or to limit embodiments hereof in any way. One should appreciate that the above-described features can be combined in any manner that makes technological sense, and that all such combinations are intended to be disclosed herein, regardless of whether such combinations are identified explicitly or not.

BRIEF DESCRIPTION OF THE SEVERAL VIEWS OF THE DRAWINGS

The foregoing and other features and advantages will be apparent from the following description of particular embodiments, as illustrated in the accompanying drawings, in which like reference characters refer to the same or similar parts throughout the different views. The drawings are not necessarily to scale, emphasis instead being placed upon illustrating the principles of various embodiments.

DETAILED DESCRIPTION

Embodiments of the improved technique will now be described. One should appreciate that such embodiments are provided by way of example to illustrate certain features and principles but are not intended to be limiting.

An improved technique for testing a pushrod valvetrain in an engine includes replacing an original pushrod with an instrumented pushrod (IPD) that includes a sensor configured to measure strain and/or motion. The engine is then operated, and the output of the sensor is monitored for anomalies. Diagnosis and repair of identified defects may then be performed.

Figure 1:
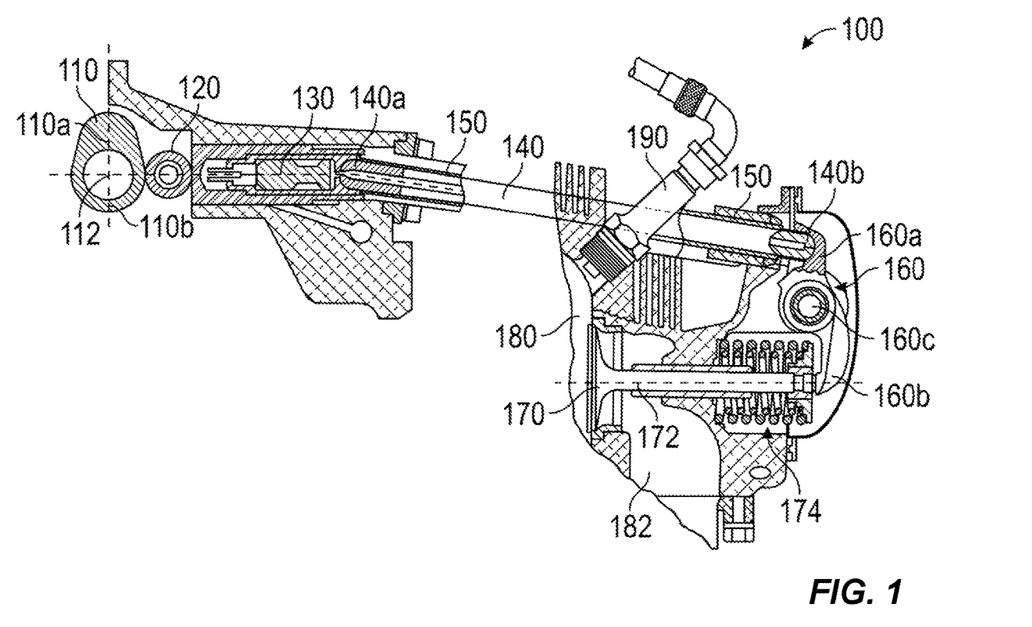
FIG. 1 is a partial, cross-sectional view of an example engine that includes a valvetrain that uses a pushrod.

FIG. 1 shows an example pushrod valvetrain 100 in which embodiments of the improved technique can be practiced. As shown, the valvetrain 100 includes a cam 110 configured to rotate about a camshaft 112, which provides an axis of rotation for the cam 110. The cam 110 has an eccentric profile, with a more eccentric region 110a and a less eccentric region 110b. The cam 110 is arranged to push against a tappet 120 (e.g., a round or flat tappet), and the tappet 120 is arranged to push against a lash adjuster 130. The lash adjuster 130 is configured to remove lash (or slack) from mechanical connections. The lash adjuster 130 is coupled to a first end 140a of a pushrod 140. The pushrod 140 is disposed within a shroud tube 150 and is configured to move back and forth within the shroud tube 150. Although shown only at its ends, the shroud tube 150 extends over the entire length of the pushrod 140. The pushrod 140 extends to a second end 140b, which is coupled to a rocker assembly 160. The rocker assembly 160 has a first end 160a that contacts the pushrod 140 and a second end 160b that contacts a valve stem 172 of a valve 170. The rocker assembly 160 is configured to pivot about a rocker shaft 160c. The valve 170 is arranged to open and close, to selectively allow intake or exhaust gases to pass between a combustion chamber 180 and an intake or exhaust port 182. A valve spring 174 (which may be an assembly of multiple springs) is configured to bias the valve 170 closed. The same general components may be used for both intake and exhaust valves. Also shown is a spark plug 190.

In example operation, the camshaft 112 rotates, causing the cam 110 to present a profile to the tappet 120 that alternates between the more eccentric region 110a and the less eccentric region 110b. As the more eccentric region 110a pushes against the tappet 120, the pushrod 140 advances, via the lash adjuster 130, against the first end 160a of the rocker assembly 160, which pivots about the rocker shaft 160c and causes the second end 160b of the rocker assembly 160 to push against the valve stem 172, pushing the valve 170 open and allowing gases to pass between the combustion chamber 180 and the port 182. As the cam 110 rotates past the angle of maximum eccentricity, the valve spring 174 pushes the valve 170 closed and pushes back on the pushrod 140, allowing substantial contact to be maintained between the pushrod 140 and the tappet 130 (via the lash adjuster 130), and between the tappet 120 and the cam 110. Operation continues in this fashion in a cyclic manner, with the valve 170 opening and closing in synchronization with the rotation of the cam 110.

Figure 2:
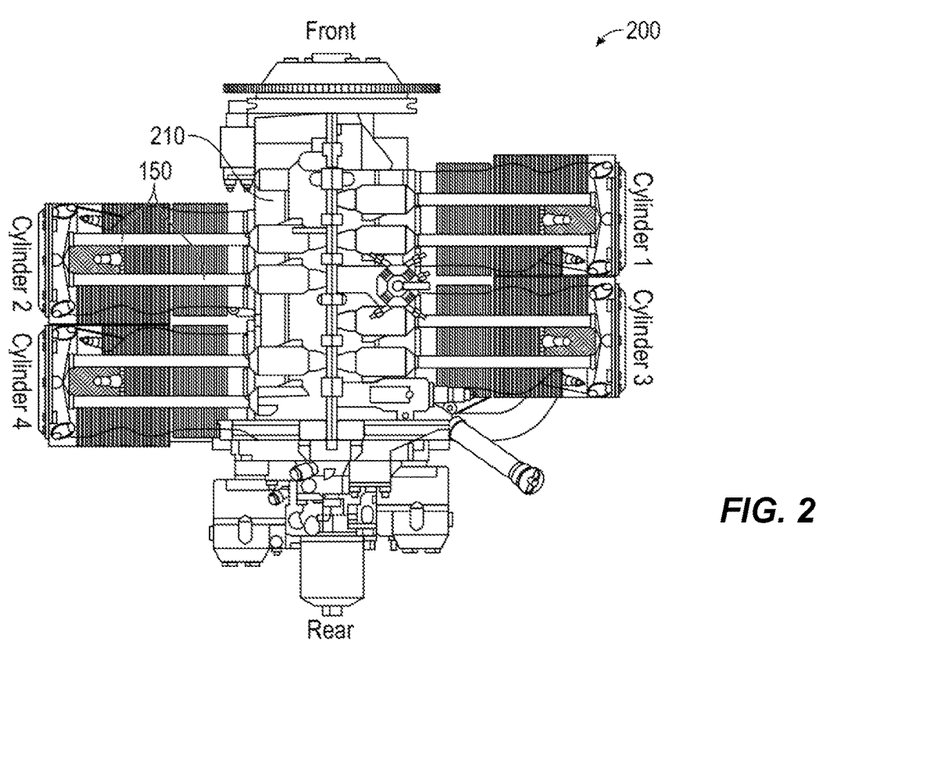
FIG. 2 is a top plan view of an engine that uses pushrods, such as the engine in which the valvetrain is found in FIG. 1.

FIG. 2 shows an example of an engine 200 which may include the valvetrain 100 of FIG. 1. The engine 200 is seen to have four cylinders and eight valves, i.e., one intake valve and one exhaust valve per cylinder. Eight shroud tubes 150 are shown, with each shroud tube enclosing a respective pushrod 140. In the example, camshaft 112 is disposed within a central region 210 of the engine 200 and extends vertically (from the perspective of the figure). Camshaft 112 has multiple cams 110 attached thereto. The cams 110 are oriented at angles that establish desired timing characteristics for opening and closing the valves 170. One should appreciate that the depicted engine 200 is merely an example provided for illustration. For instance, embodiments may be practiced using engines having different numbers of cylinders provided in arrangements different from that shown. Also, pushrods need not extend externally to a main portion of the engine, as shown, although the external arrangement may provide the greatest advantages.

Figure 3:
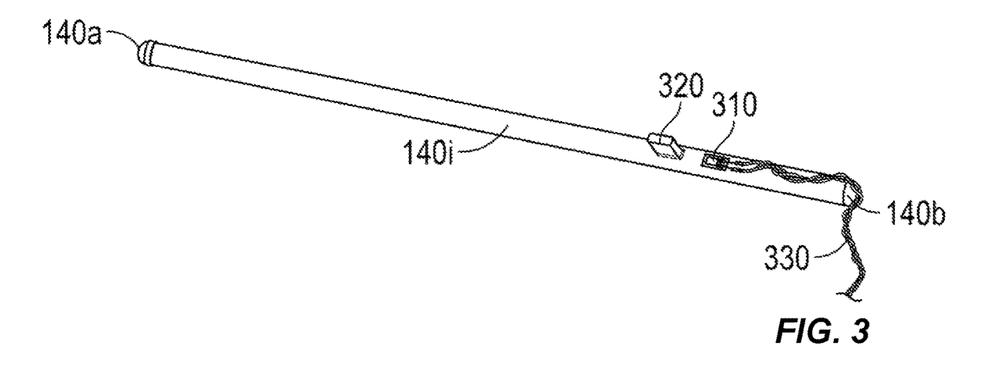
FIGS. 3-5 are plan views of examples of instrumented pushrods in accordance with improvements hereof.
Figure 4:
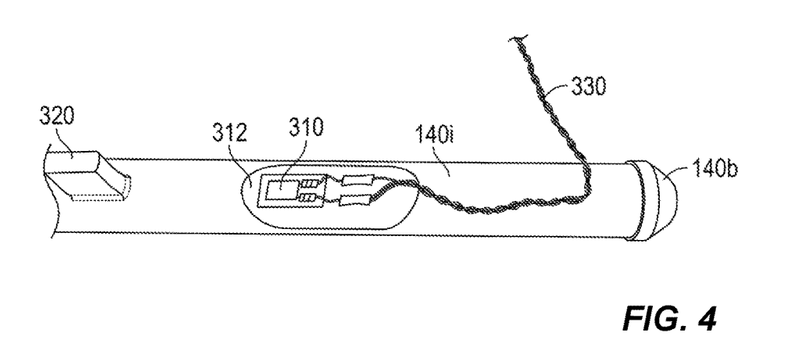
Figure 5:
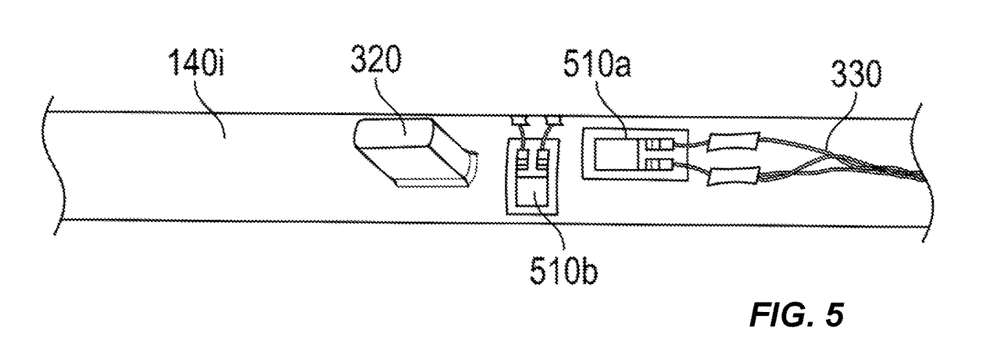

FIGS. 3-5 show examples of an instrumented pushrod (IPD) 140i in accordance with improvements hereof. The IPD 140i may be a modified version of a conventional pushrod used by the engine being evaluated. For example, the IPD 140i may have the same size and shape and be composed of the same materials as pushrods normally used for the type of engine. However, the IPD 140i may be composed of any suitable materials.

The IPD 140i includes a sensor 310 and a guide 320. Wires 330 may extend from the sensor to carry electrical signals to a measurement station. The sensor 310 may include any number of sensing devices and is attached to a side of the IPD 140i, e.g., at a location near the end 140b (the end closest to the rocker assembly 160), to allow for easy access. In an example, the sensor 310 is bonded to an outer surface of the IPD 140i, e.g., using epoxy 312. The epoxy 312 or other bonding material may cover the wires 330 over a length of at least one centimeter or so, to provide strain relief for protecting the sensor 310. A boot or other wire protector may be used in place of, or in addition to, the epoxy 112 for protecting the sensor 310 and wires 330. The wires 330 may be held against the IPD 140i for some distance such that they turn away from the IPD 140i at a determined location, which may be selected based on geometrical constrains within the engine 200 and with an eye toward preventing chafing or other damage to the wires 330.

In one example, the sensor 310 includes a strain gauge configured to measure axial strain along the length of the IPD 140i. In this case, the wires 330 convey low-level electrical signals that vary in relation to applied strain. In some examples, the sensor 310 may include first and second strain gauges 510a and 510b (FIG. 5), which are oriented at right angles to each other. For example, the first strain gauge 510a is oriented axially and the second strain gauge 510b is oriented circumferentially (sideways). The second strain gauge 510b may be used for compensating measurements made by the first strain gauge 510a for temperature. Although not shown, the second strain gauge 510b may also have wires that extend therefrom, which are also conveyed to the measurement station. Each strain gauge may be of any suitable type, such as a linear strain gauge, a membrane Rosette strain gauge, a double linear strain gauge, a full bridge strain gauge, a hear strain gauge, a half bridge strain gauge, a column strain gauge, or a 45°-Rosette strain gauge, for example.

In some examples, the sensor 310 includes one or more accelerometers, which are configured to measure acceleration in at least an axial direction, i.e., along the length of the IPD 140i. An accelerometer may be provided in place of, or in addition to, one or more strain gauges. In the usual manner, velocity may be computed as the integral of acceleration, and displacement may be computed as the double-integral of acceleration.

Figure 6:
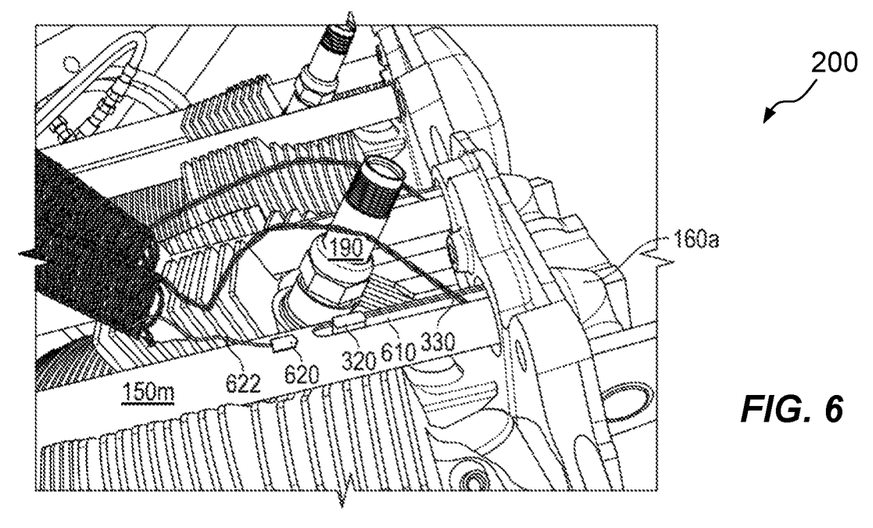
FIGS. 6 and 7 are perspective views of portions of an engine equipped with instrumented pushrods and modified shroud tubes.
Figure 7:
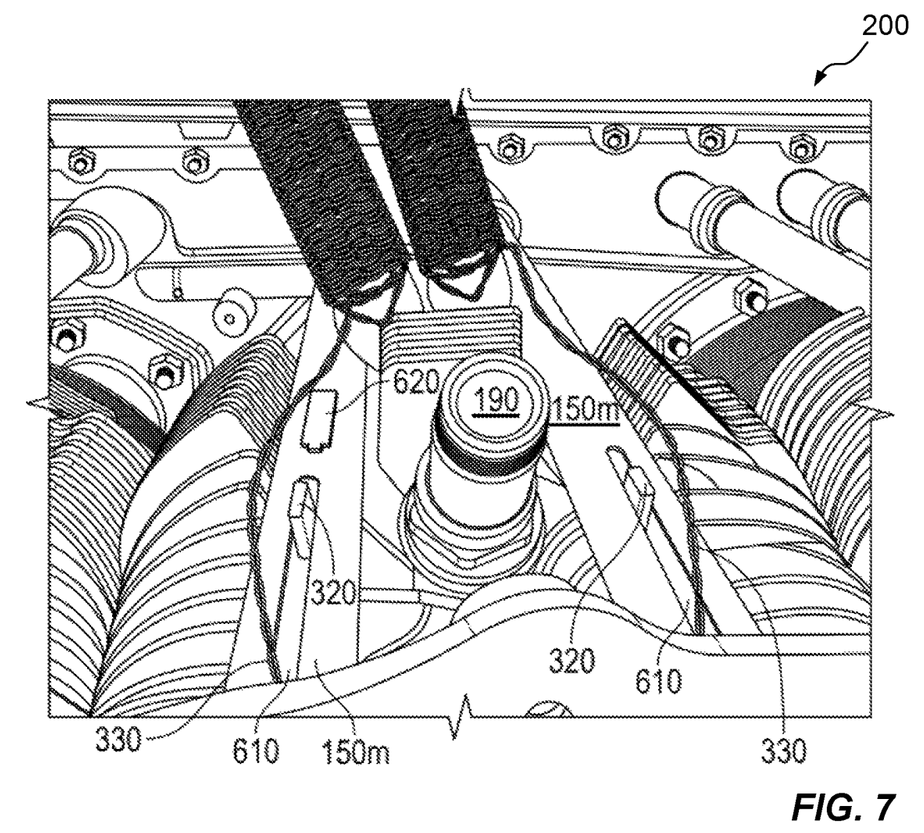

The guide 320 extends laterally from the IPD 140i and is configured to engage an aperture, such as a slot, within a modified shroud tube (FIGS. 6 and 7). In an example, the guide 320 is provided as a tab or pin affixed to a side of the IPD 140i, e.g., by welding or soldering or by using an adhesive or fastener, such as one or more screws or rivets. The guide 320 is preferably composed of metal but may alternatively be composed of durable, heat-resistant plastic. As yet another example, a hole may be drilled in the side of IPD 140i and a dowel may be inserted into the hole. The dowel may form an interference fit with the hole, or it may be welded, adhered, fastened, or soldered in place.

FIGS. 6 and 7 show an example of IPDs 140i installed within modified shroud tubes 150m of engine 200. As few as one and as many as eight IPD's 140i may be installed in the engine 200 (i.e., one per valve). Guides 320 of the IPDs 140i can be seen extending from slots 610 formed in respective modified shroud tubes 150m. The slots 610 serve the dual purposes of preventing rotation of the respective IPDs and of providing a path for wires 330 to exit from the modified shroud tubes 150m. In an example, each slot 610 extends to the end of the respective shroud tube 150m to allow for easy insertion of the IPD and its guide 320 into the shroud tube 150m. Each slot 610 also extends a distance down the shroud tube 150m sufficient to accommodate a maximum extent of travel of the IPD 140i as the respective valve 170 opens and closes.

In some examples, a proximity sensor 620 may be attached to a shroud tube 150 for monitoring a proximity of the guide 320 as it moves back and forth within the shroud tube 150m during engine operation. For example, an inductive proximity sensor may be used with guides 320 made of metallic material (e.g., steel), or a capacitive proximity sensor may be used with guides 320 made of non-metallic material (e.g., plastic). Wires 622 may connect the proximity sensor 620 to the measurement station.

One should appreciate that engine oil typically circulates through the shroud tubes 150m during engine operation. In some examples, a plastic shield or tube (not shown) may be applied around each modified shroud tube 150m in the vicinity of the slot 610 to contain oil spray when operating the engine 200. Also, portions of each slot 610 where the guide 320 does not extend may be temporarily sealed.

Figure 8:
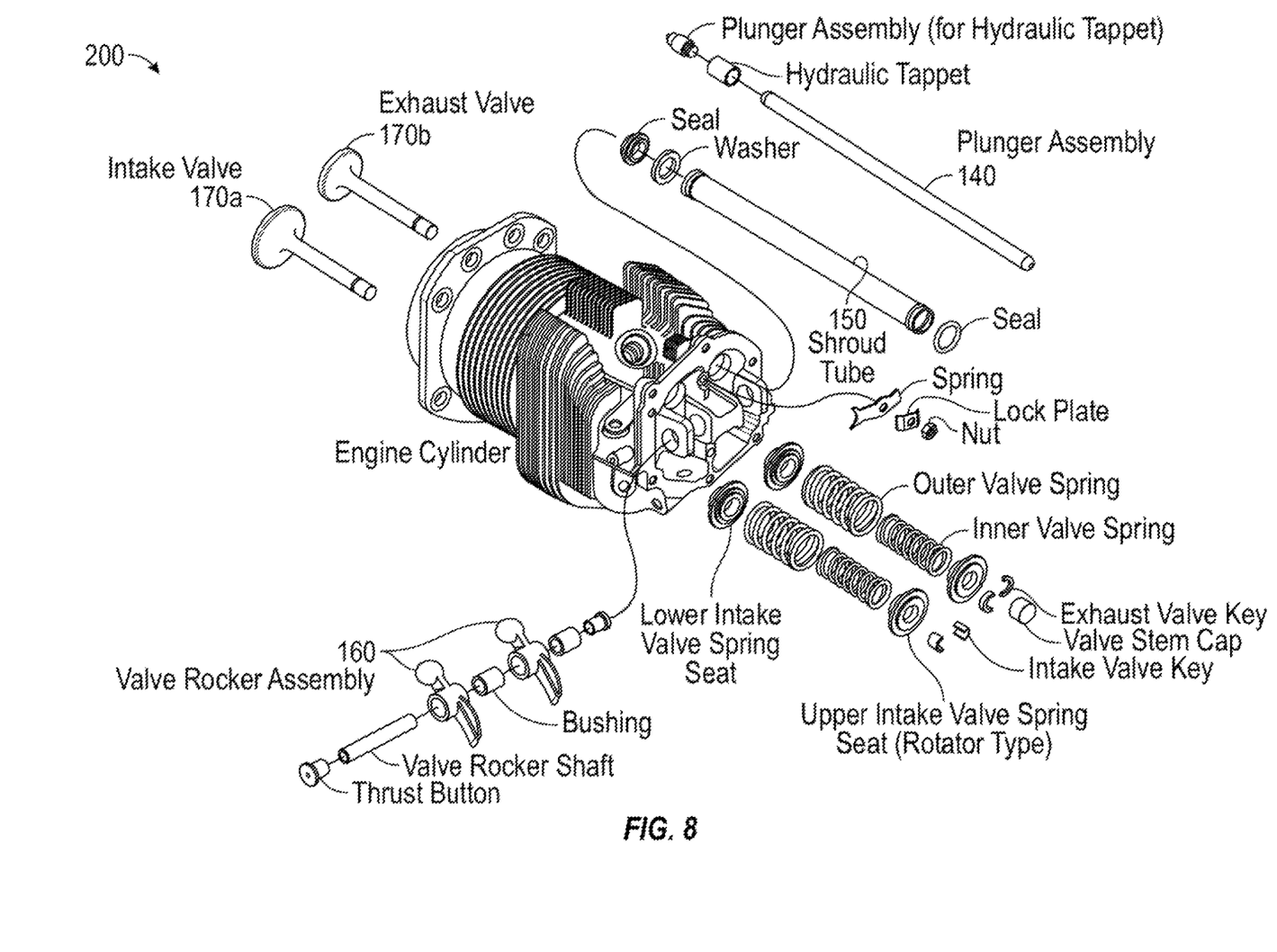
FIG. 8 is an exploded view of a cylinder of an example engine that uses pushrods, such as that shown in FIGS. 1, 2, 6, and 7.

FIG. 8 is an exploded view of the engine 200 prior to installing the IPD 140i and modified shroud tube 150m. It is apparent from FIG. 8 that the disclosed modifications may be easily performed, given the accessibility of the shroud tube 150 outside a main body of the engine. It is expected that a skilled mechanic would require no more that several minutes per valve to complete the modifications.

Figure 9:
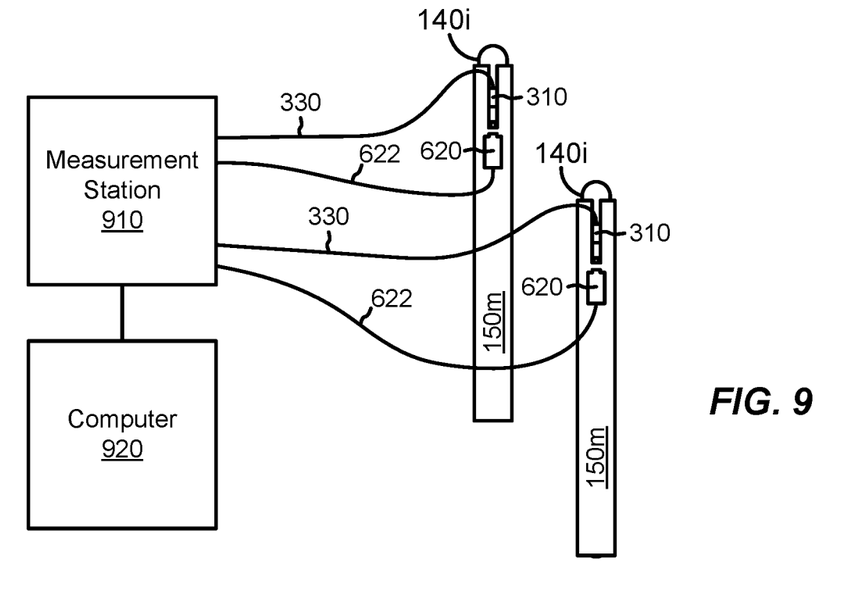
FIG. 9 is a block diagram that shows example electrical connections between modified pushrods and external measurement equipment.

FIG. 9 shows an example setup for measuring valvetrain performance. The depicted setup includes one or more IPDs 140i installed within respective modified shroud tubes 150m, as well as a measurement station 910 and a computer 920. Wires 330 from the sensors 310 on the respective IPDs 140i connect to measurement ports in the measurement station 910, as do wires 622 from the proximity sensors (if provided). The measurement station 910 may include circuitry for amplifying signals from strain gauges, accelerometers, and/or proximity sensors, and for digitizing the amplified signals at a determined rate.

A suitable example of the measurement station 910 is a DAQ chassis available from National Instruments Corporation of Austin, TX For example, the DAQ chassis may include terminals for connecting to strain gauges, accelerometers, and proximity sensors. Measurements made by the measurement station 910 may be recorded and viewed using the computer 920.

In example operation, the IPDs 140i and shroud tubes 150m are installed in the engine 200 and the measurement station 910 is operated to obtain measurements of signals that are output by the sensors 310 and proximity sensors 620 as the engine runs. The computer 920 may record and display the measurements. In some examples, the computer 920 runs software that also performs signal analysis. The software may be programmed to detect anomalies in output signals, such as deviations that correspond to weak or worn valve springs, contaminated engine oil, hydraulic lash adjuster failure, excessive valvetrain clearances, and/or other issues. In some examples, the software is configured to generate pass or fail results, e.g., on a per-valve basis. The software may further be configured to provide more detailed results. The results may include diagnoses of particular anomalies detected. The diagnoses may be based, for example, on comparisons of signals from an IPD 140i with those of a pushrod in an ideal valvetrain, such as a simulated valvetrain with no defects. The results may also include comparisons of signals from an IPD 140i with signals obtained from a known-good, real-world valvetrain, which may serve as a golden test standard.

Figure 10:
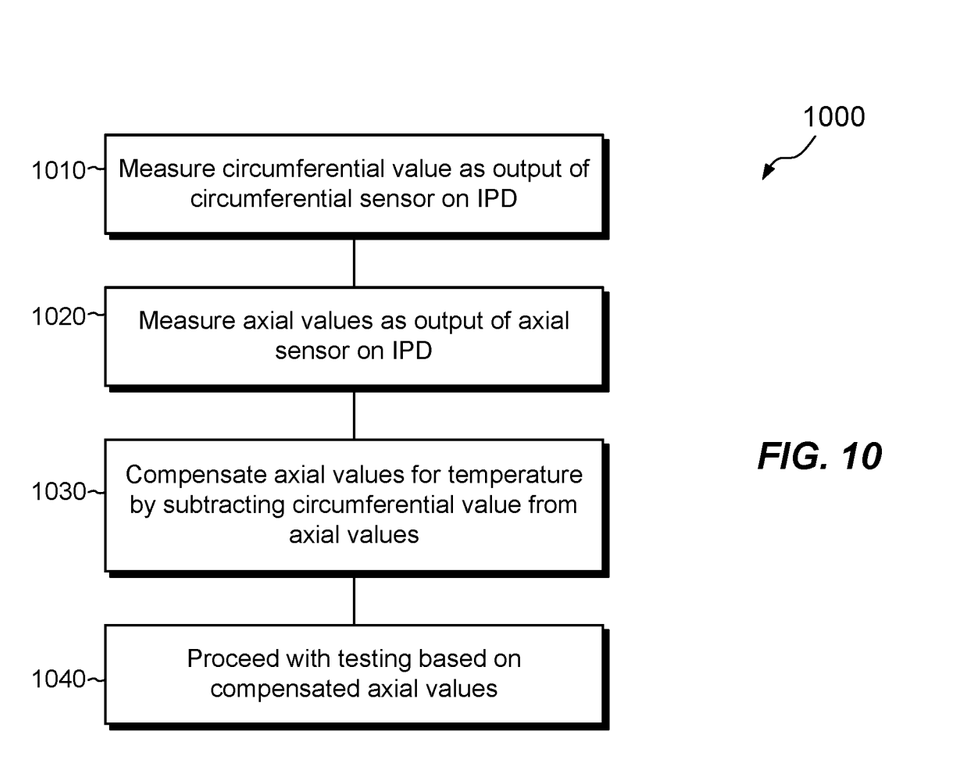
FIG. 10 is a flowchart that shows an example method of compensating for temperature variations when measuring strain from sensors on an IPD.

FIG. 10 shows an example method 1000 of compensating strain measurements for temperature in the arrangement of FIG. 9. Method 1000 may be performed, for example, by the computer 920 working in connection with the measurement station 910, based on strain measurements obtained by strain gauges provided in the sensors 310. The depicted steps of method 1000 may be carried out in any suitable order.

It has been observed that IPDs 140i are susceptible to temperature variations of hundreds of degrees Fahrenheit. Such variations can cause large changes in outputs of strain gauges provided in sensors 310. Large values of measured strain may thus be the result of temperature changes in addition to mechanical forces applied to the IPDs.

To distinguish mechanically-induced strain from temperature effects, an IPD 140*i* may employ two strain gauges 510*a* and 510*b* (FIG. 5). In such cases, both strain gauges 510*a* and 510*b* may be wired to the measurement station 910.

At step 1010 of method 1000, a circumferential strain value is measured from strain gauge 510*b*. Given that no substantial circumferential mechanical forces are expected in an IPD 140*i*, substantially all of the measured strain from strain gauge 510*b* may be attributed to temperature.

At step 1020, axial strain may be measured from strain gauge 510*a*. For strain gauge 510*a*, it is expected that measurements of strain are based on both temperature and mechanically-induced forces.

At step 1030, the axial measurement made by strain gauge 510*a* is compensated for temperature by subtracting the measurement from strain gauge 510*b* from that of strain gauge 510*a*. Following the subtraction, substantially all of the strain indicated by strain gauge 510*a* is attributable to mechanically-induced forces, with substantially none of it attributable to temperature.

At step 1040, valvetrain testing proceeds based on the temperature-compensated strain measurements, i.e., those obtained after the subtracting step 1030.

In some examples, a new circumferential strain measurement is made from strain gauge 510*b* each time a new measurement is taken from strain gauge 510*a*. This is not required, however. For example, measurements from strain gauge 510*b* may be taken periodically, with each measurement used for correcting multiple measurements from strain gauge 510*a*, i.e., for some interval of time over which temperature is not expected to change significantly. In some examples, multiple measurements of strain gauge 510*b* may be taken in rapid succession and averaged together (to reduce noise), with the resulting average value applied during the subtracting step 1020. Measurements from strain gauge 510*a* may also be averaged. In some examples, a correction factor is applied to circumferential measurements when subtracting, to account for the difference between axial and circumferential thermal expansion of the cylindrically-shaped IPD 140*i*. The correction factor may take the form of a coefficient, for example. Numerous variations of the above approach are contemplated, with the specific examples described not intended to be limiting.

Figure 11:
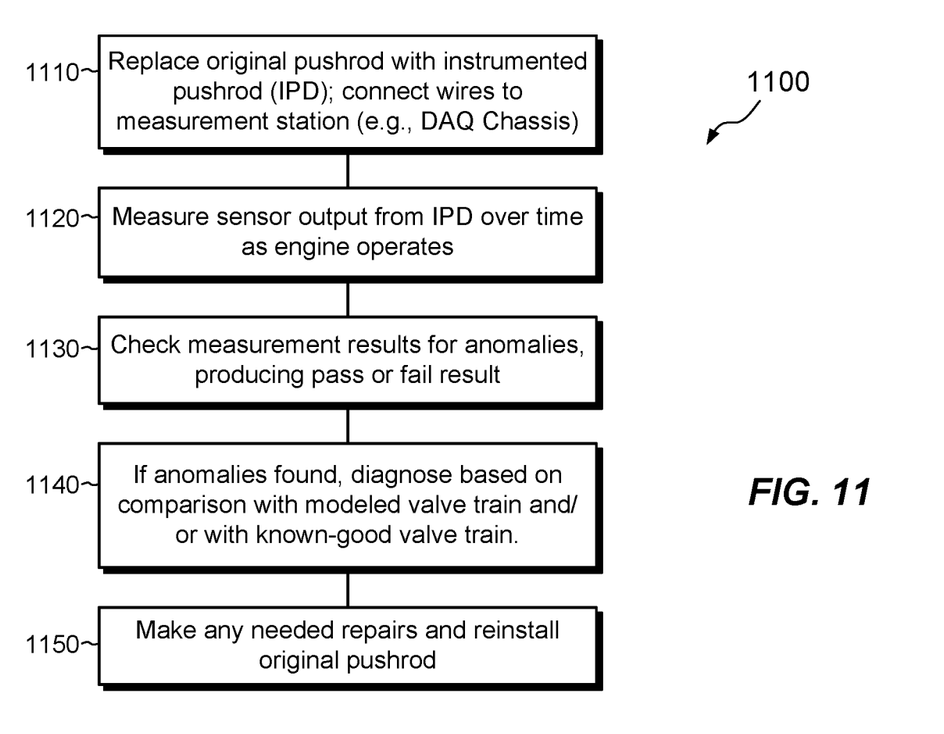
FIG. 11 is a flowchart that shows an example method of testing and/or characterizing a valvetrain using one or more instrumented pushrods.

FIG. 11 shows an example method 1100 of testing and/or characterizing a valvetrain 100 in an engine 200 using an IPD 140*i*. The method 1100 may be carried out, for example, by human repair personnel and by the test station 910 and computer 920 of FIG. 9. The various acts of method 1100 may be ordered in any suitable way. Accordingly, embodiments may be constructed in which acts are performed in orders different from that illustrated, which may include performing some acts simultaneously.

At 1110, an original pushrod 140 of a valvetrain 100 of an engine 200 is replaced with an IPD 140*i*. Any number of original pushrods (up to one per valve) may be replaced with respective IPDs 140*i*. Wires from sensor(s) 310 are connected to measurement station 910. If modified shroud tubes 150*m* include proximity sensors 620, wires from any such proximity sensors 620 may also be connected to the measurement station 910.

At 1120, outputs of sensors 310 (and of proximity sensor 620, if provided) are measured over time as the engine 200 operates. For example, measurements are acquired by measurement station 910 and are recorded by computer 920.

At 1130, measurement results are checked for anomalies. For example, computer 920 may run software that implements an automated test procedure. The test procedure may produce a pass result or a fail result.

At 1140, fault diagnosis may proceed if one or more anomalies are found. Such diagnosis may be based, for example, on a comparison between the recorded measurements and those of an ideal valvetrain, or a known-good, "golden," valvetrain.

At 1150, any identified faults may be addressed, such as by repairing or replacing any defective components. The original pushrod(s) 140 and shroud tube(s) 150 may be put back in place, and the engine 200 may be returned to service.

An improved technique has been described for testing a pushrod valvetrain in an engine. The technique includes replacing an original pushrod of the valvetrain with an instrumented pushrod (IPD) which includes a sensor configured to measure strain and/or motion. The engine is then operated with the IPD in place, and the output of the sensor is monitored for anomalies. Diagnosis and repair of identified defects may then follow.

Having described certain embodiments, numerous alternative embodiments or variations can be made. For example, although embodiments have been described that employ wired sensors 310, other embodiments may include wireless sensors. For example, an instrumented pushrod may be adapted to include a Bluetooth or other wireless sensor (e.g., Wi-Fi, IR, etc.), thus avoiding the need for an aperture in the modified shroud tube 150*m* and the consequent emission of oil. The guide 320 and slot 610 can thus be omitted. Instead, a modified shroud tube 150*m* may be constructed of an electromagnetically transparent material, or it may include an electromagnetically transparent window to allow for wireless communication.

Additional embodiments may replace the measurement station 910 and computer 920 with a test box that includes the required electronics for measuring outputs of the sensors and determining a pass/fail result.

Further, although features have been shown and described with reference to particular embodiments hereof, such features may be included and hereby are included in any of the disclosed embodiments and their variants. Thus, it is understood that features disclosed in connection with any embodiment are included in any other embodiment.

Further still, portions of the improved technique may be embodied as a computer program product including one or more non-transient, computer-readable storage media, such as a magnetic disk, magnetic tape, compact disk, DVD, optical disk, flash drive, solid state drive, SD (Secure Digital) chip or device, Application Specific Integrated Circuit (ASIC), Field Programmable Gate Array (FPGA), and/or the like. Any number of computer-readable media may be used. The media may be encoded with instructions which, when executed on one or more computers or other processors, perform the process or processes described herein. Such media may be considered articles of manufacture or machines, and may be transportable from one machine to another.

As used throughout this document, the words "comprising," "including," "containing," and "having" are intended to set forth certain items, steps, elements, or aspects of something in an open-ended fashion. Also, as used herein and unless a specific statement is made to the contrary, the word "set" means one or more of something. This is the case regardless of whether the phrase "set of" is followed by a singular or plural object and regardless of whether it is conjugated with a singular or plural verb. Also, a "set of"

elements can describe fewer than all elements present. Thus, there may be additional elements of the same kind that are not part of the set. Further, ordinal expressions, such as "first," "second," "third," and so on, may be used as adjectives herein for identification purposes. Unless specifically indicated, these ordinal expressions are not intended to imply any ordering or sequence. Thus, for example, a "second" event may take place before or after a "first event," or even if no first event ever occurs. In addition, an identification herein of a particular element, feature, or act as being a "first" such element, feature, or act should not be construed as requiring that there must also be a "second" or other such element, feature or act. Rather, the "first" item may be the only one. Also, and unless specifically stated to the contrary, "based on" is intended to be nonexclusive. Thus, "based on" should be interpreted as meaning "based at least in part on" unless specifically indicated otherwise. Although certain embodiments are disclosed herein, it is understood that these are provided by way of example only and should not be construed as limiting.

Those skilled in the art will therefore understand that various changes in form and detail may be made to the embodiments disclosed herein without departing from the scope of the following claims.

What is claimed is:

1. A method of testing a pushrod valvetrain of an internal combustion engine, comprising:
    replacing a pushrod of the engine with an IPD (instrumented pushrod) that includes a sensor configured to measure strain and/or motion, the IPD configured to move back and forth within a tube and including a guide configured to move back and forth within a slot of the tube;
    operating the engine in a fired arrangement with the IPD in place; and
    monitoring the output of the sensor to identify anomalies.

2. The method of claim 1, wherein monitoring the output of the sensor to identify anomalies includes comparing output from the sensor with that of a modeled, ideal valvetrain and identifying discrepancies.

3. The method of claim 1, further comprising receiving electrical signals from sensor, digitizing the electrical signals, and recording the electrical signals for analysis and/or viewing.

4. The method of claim 1, wherein the tube includes a proximity sensor, and wherein the method further comprises monitoring, by the proximity sensor, a position of the guide as the guide moves back and forth within the slot.

5. The method of claim 1, wherein the sensor includes a first strain gauge oriented axially with the IPD to measure axial strain, wherein the IPD further includes a second strain gauge oriented perpendicularly to the first strain gauge, and wherein the method further comprises applying strain measurements from the second strain gauge to compensate output of the first strain gauge for variations in temperature.

6. The method of claim 1, further comprising replacing a second pushrod of the engine with the IPD, operating the engine in a fired arrangement with the IPD in place of the second pushrod, and monitoring the output of the sensor to identify additional anomalies.

7. The method of claim 1, wherein the IPD is one of a plurality of IPDs that replace respective pushrods of the engine, each of the plurality of IPDs having a sensor, and wherein the method further comprises:
    operating the engine in a fired arrangement with the plurality of IPDs in place; and
    monitoring the output of the sensor of each of the plurality of IPDs to identify anomalies.

8. The method of claim 1, wherein the sensor is configured to communicate wirelessly with a test station, and wherein monitoring the output of the sensor includes receiving, by the test station, wireless signals from the sensor.

9. An apparatus for testing a pushrod valvetrain of an internal combustion engine, comprising:
    an IPD (instrumented pushrod) that includes a guide that extends radially outwardly from the IPD and a sensor configured to measure strain and/or motion;
    a tube within which the IPD is constructed and arranged to move back and forth when the engine is operated; and
    a measurement station constructed and arranged to receive measurements from the sensor and to identify anomalies in the measurements,
    wherein the tube includes a slot within which the guide is constructed and arranged to move back and forth when the engine is operated.

10. The apparatus of claim 9, wherein the measurement station constructed and arranged to receive measurements from the sensor is further constructed and arranged to receive the measurements in wireless signals transmitted by the sensor.

11. The apparatus of claim 9, further comprising a set of wires that extends through the slot from the sensor to the measurement station.

12. The apparatus of claim 9, wherein the tube includes a proximity sensor constructed and arranged to measure a position of the guide as the guide moves back and forth within the slot.

13. The apparatus of claim 12, wherein the guide comprises a metallic material, and wherein the proximity sensor comprises an inductive sensor.

14. The apparatus of claim 12, wherein the guide comprises a non-metallic material, and wherein the proximity sensor comprises a capacitive sensor.

15. The apparatus of claim 9, wherein the sensor includes a first strain gauge, wherein the IPD includes a second strain gauge oriented perpendicularly to the first strain gauge, and wherein the apparatus further includes a second set of wires extending through the slot between the second strain gauge and the measurement station.

16. An instrumented pushrod (IPD), comprising:
    an elongated rod;
    a sensor attached to or integral with the elongated rod, the sensor constructed and arranged to measure strain and/or motion; and
    a guide that extends radially outwardly from the elongated rod, the guide constructed and arranged to resist rotation of the elongated rod during engine operation.

17. The IPD of claim 16, wherein the sensor is bonded to the elongated rod using epoxy.

18. The IPD of claim 16, further comprising:
    a set of wires that attach to the sensor, the set of wires extending axially over a portion of the elongated rod; and
    a retainer constructed and arranged to hold the set of wires against the elongated rod over the portion of the elongated rod.

19. The IPD of claim 16, wherein the sensor includes a first strain gauge, and wherein the IPD further comprises a second strain gauge oriented perpendicularly to the first strain gauge.

20. The IPD of claim 16, wherein the guide is attached to or integral with the elongated rod.

* * * * *